United States Patent [19]

LeVeen et al.

[11] Patent Number: 4,532,936
[45] Date of Patent: Aug. 6, 1985

[54] AUTOMATIC URINE FLOW METER

[76] Inventors: Eric G. LeVeen, 321 Confederate Cir., Charleston, S.C. 29407; Robert F. LeVeen, 312 Lombard St., Philadelphia, Pa. 19147

[21] Appl. No.: 295,073

[22] Filed: Aug. 21, 1981

[51] Int. Cl.$^3$ ............................................. A61M 1/00
[52] U.S. Cl. ................................. 128/762; 128/768; 128/771; 604/67; 604/246; 604/317; 604/323
[58] Field of Search ............. 128/771, 295, 760, 761, 128/762, 767, 768; 604/67, 151, 153, 245, 246, 317, 323

[56] References Cited
U.S. PATENT DOCUMENTS

| | | | |
|---|---|---|---|
| 3,769,497 | 10/1973 | Frank | 128/295 X |
| 3,818,895 | 6/1974 | Stewart | 128/771 X |
| 4,343,316 | 8/1982 | Jespersen | 128/771 |
| 4,381,776 | 3/1983 | Latham | 604/317 |

OTHER PUBLICATIONS

Chambers et al., Med. and Biol. Engr., vol. 14, No. 6, Nov. 1976, pp. 665–669.

*Primary Examiner*—Kyle L. Howell
*Assistant Examiner*—John C. Hanley
*Attorney, Agent, or Firm*—Gipple & Hale

[57] ABSTRACT

The present inventive apparatus measures the output of urine optically, totalizes it and prints it on a self-adherent paper which can easily be afixed to the hospital chart. The apparatus includes a measurement column, an optical sensor to determine when the measurement column is empty, a peristaltic pump to empty the measurement column at a known rate, into a collection bag or specimen bottle and control logic to determine the volume removed from the column based on the pump rate. A display is also provided for easy observation of current output statistics. Specimens can be collected under automatic or manual control for biochemical analysis without contamination by contact or alteration by electrical current. An alarm may be sounded when the collection bag is in need of replacement, or when the urine output falls or rises to predetermined rates.

4 Claims, 4 Drawing Figures

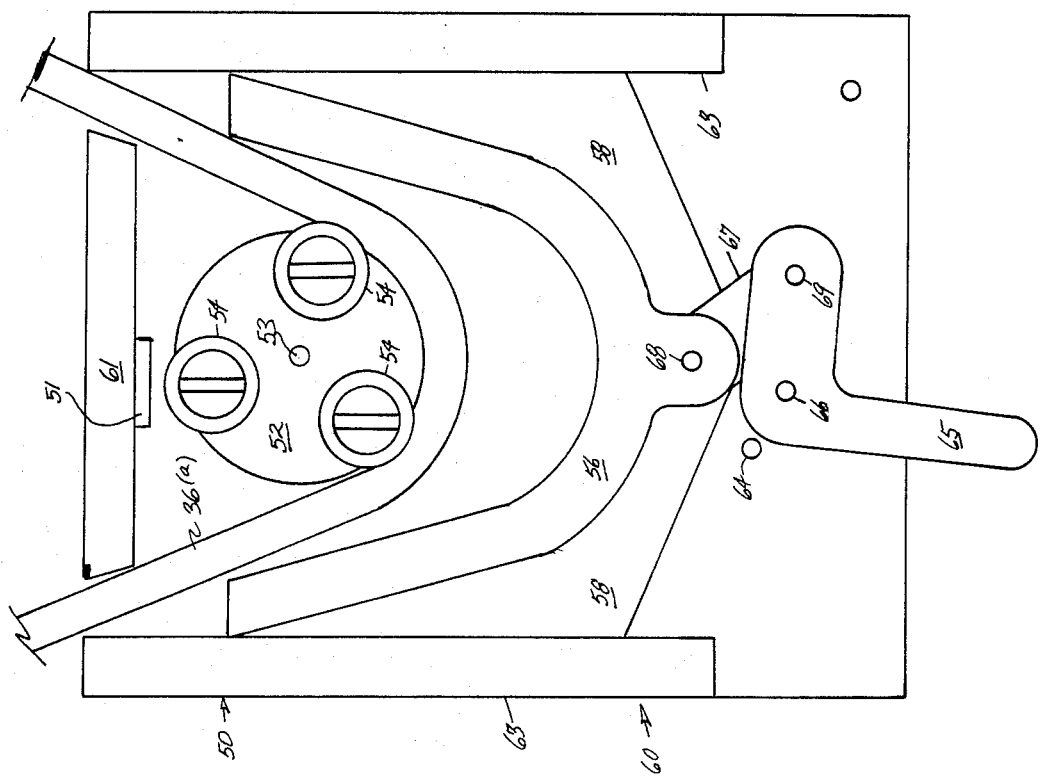
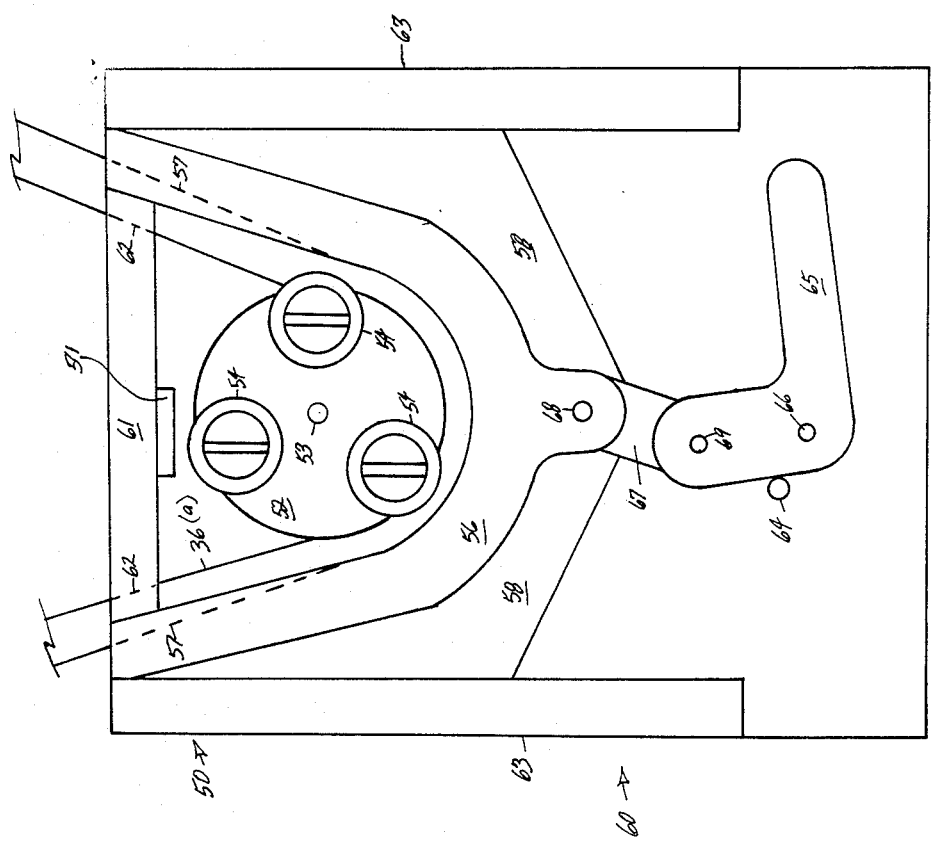

AUTOMATIC URINE FLOW METER

BACKGROUND OF THE INVENTION

The present inventive system relates to fluid output measurement, and more specifically to an automatic urinary output measurement and recording mechanism.

In seriously ill patients, it is often necessary to measure the hourly urinary output. This output gives a great deal of information about the function of various body systems such as the cardiovascular system. If the blood pressure were to fall, the urinary output would diminish or cease depending upon the severity of the blood pressure drop. The kidney is very susceptible to damage during periods of anoxia, shock, severe trauma, bacterial infections or transfusion of incompatible blood. If the kidneys are seriously damaged, renal output may cease for periods of days to weeks before restoration. In addition, to assertain and manage the fluid balance of critically ill patients, it is necessary to know the extent of their urinary loss. If renal insufficiency ensues, this is usually detectable by a marked increase in the urinary output or a striking decrease in the urinary output. These two conditions have sometimes been designated as high output and low output renal failure. Sometimes the renal failure is merely functional and not pathological. Monitoring the urinary output alerts the physician when functional failure is not longer a threat. If urinary output falls beneath 30 cc's per minute, the situation is called oliguria. Oliguria may not respond to a simple increase in fluid intake by parenteral or oral route. Under these circumstances, the urinalysis may aid in determining whether the problem is simply one of under perfusion of the kidneys or of pathological damage. This can often be determined by sodium content of the urine. In patients with acute tubular necrosis, the urinary sodium levels are high while patients whose kidneys are simply under perfused have a low urinary sodium value.

One of the prime functions of the kidney is to concentrate the excretory waste material. To accomplish this, the kidneys must do osmotic work. Therefore, osmolarity of the urine is the best kidney function test that is available. It may be necessary to repeatedly follow the osmolarity of the urine to determine whether the kidneys are recovering and how seriously they are injured. Seriously damaged kidneys cannot produce urine with a osmolarity greater than 300 mil osmols per liter. In patients with elevated urea nitrogen levels and high urinary outputs, it is not uncommon to find that the kidney is unable to do osmotic work. If recovery occurs, urinary osmolarity rises and often diuresis ceases. In diabetic acidosis, it may be necessary to measure the hourly composition of the urine with respect to glucose and ketone bodies to make the necessary adjustments in insulin dosage and to determine the extent of recovery from the diabetic acidosis.

Urinary collection is usually done by inserting a catheter into the bladder and collecting the urinary output into a bag which is measured every hour and charted on the patient's records. This is, of course, not only time consuming and costly but it wastes personnel time. What is more important is that the time required to make accurate measurements exceeds the time available to do so and frequently the information required is not collected on an hourly basis. A number of mechanical devices have been made to allow measurement of the urine on an hourly basis, but the nurse must still make the measurement and dispose of the collection.

DESCRIPTION OF THE PRIOR ART

U.S. Pat. Nos. 4,100,309 and 4,119,094, the latter being a division of the former, disclose a composition having advantageous characteristics of low friction and high flexibility for use as tubing in catheters and peristaltic pumps. In the invention, a tubular substrate is coated with a polyvinylpyrrolidone-polyurethane interpolymer which is slippery in an aqueous environment such as the body but less so when dry.

U.S. Pat. No. 3,754,220 discloses a system for monitoring the output flow from a urinary catheter. This system is limited to produce an alarm when the flow rate exceeds a predetermined value, and will not display precise values. Moreover, this system detects output by passing an electric current through fluid, which can alter the chemical and biological content of the fluid making sample analysis inaccurate. In case of system electrical faults, some current could reach the bladder itself with serious medical consequences.

Another such electrical-contact system is disclosed in U.S. Pat. No. 4,051,431. In this system the urinary output rests between capacitor plates, and acts as both a dielectric and a conductor. The resulting capacitance is measured electrically to determine the rate of flow. This system suffers the same problems as the previously-described system.

U.S. Pat. No. 3,769,497 discloses a urinary collection and measurement system in which a balanced bucket of calibrated volume receives urinary output from a patient and tips to pour the output into a collection bag when the predetermined calibrated volume has been received. A switch is coupled to the bucket and activates a counter and recorder for purposes of determining the rate of flow. This system suffers from the defect of being unable to accurately measure volumes much less than or much greater than the volume of the bucket. Furthermore, when the bucket is full, it will typically spill out only so much of its contents as is necessary to return to a balanced state. Thus the bucket will never completely empty itself, but will continually spill a small uncalibrated portion of its contents, promoting inaccuracies in measurement.

U.S. Pat. No. 2,626,385 discloses another measurement system based on conducting electric current through urinary output in a graduated cylinder. An electrode is extended partially into the cylinder so as to make contact with fluid at a level corresponding to the desired unit of output of volume to be measured. Detection circuitry is provided to detect the flow of current and operate a valve at the bottom of the graduated cylinder to release the fluid after measurement. This system not only suffers the disadvantages of electrical contact with fluid as outlined above, but also the disadvantages of a container of fixed volume which may provide accurate flow measurement only for a limited range of value.

A variety of prior art urinary output meters which require human monitoring are disclosed in U.S. Pat. Nos. 3,312,221; 3,831,446; 4,099,412; 4,238,448; and 4,241,017. Also of interest in this area are U.S. Pat. Nos. Des. 231,273; 231,865; and 240,337.

Therefore, a great need exists for a simplified apparatus to accurately measure and chart the urinary output and to make provisions for automatically collecting a urinary sample when needed. Furthermore, such a system should maintain urinary samples in an uncontaminated state and should minimize the risk of electrical shock to the patient.

SUMMARY OF THE INVENTION

The present inventive apparatus measures the output of urine optically, totalizes it and prints it on a self-adherent paper which can easily be afixed to the hospital chart. Display means is also provided for easy observation of current output statistics. There is a provision made for alarm situations if urinary output falls or rises to predetermined levels. Specimens can be collected under automatic or manual control for biochemical analysis. An alarm may be sounded when the collection bag is in need of replacement.

These and other objects and advantages of the present invention are made more readily apparent by reference to the following detailed description thereof, together with the accompanying drawings.

BRIEF DESCRIPTION OF THE DRAWINGS

FIG. 3 is an enlarged front view of a peristaltic pump advantageously incorporated in the present inventive apparatus; and FIG. 4 is a front view of the pump of FIG. 3 with the ring mechanism in a disengaged position.

DETAILED DESCRIPTION OF THE DRAWING

Figure 1:
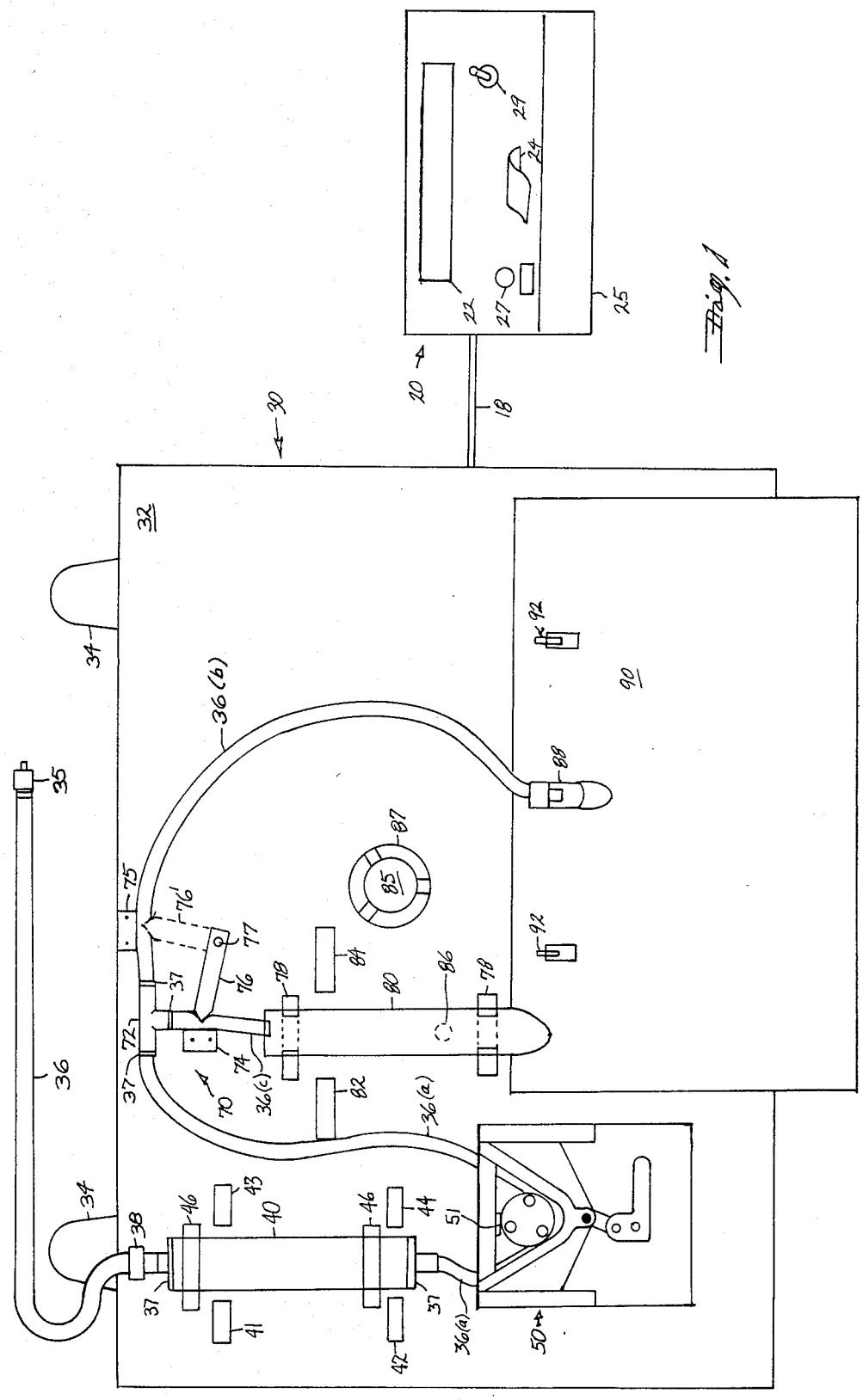
FIG. 1 is a front view of the present inventive apparatus.
Figure 2:
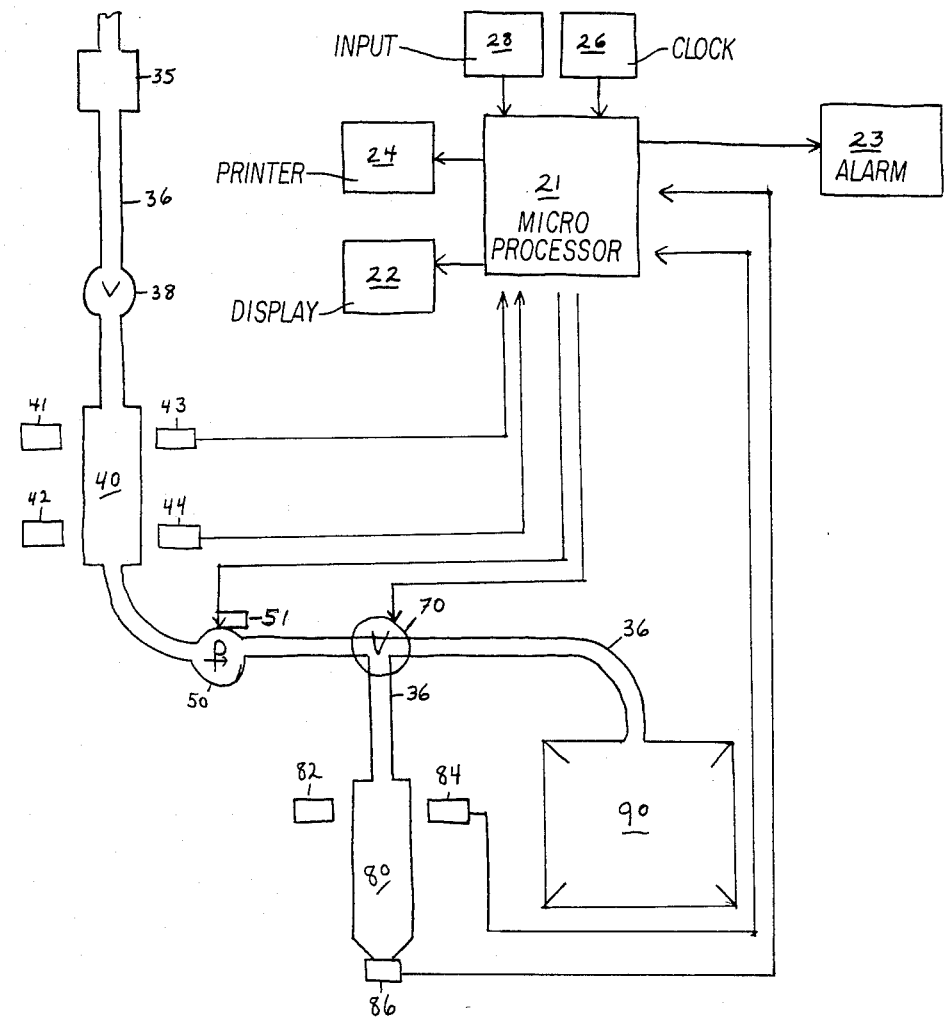
FIG. 2 is a schematic view of the apparatus of FIG. 1.

The best mode and preferred embodiment of the present invention is shown in FIGS. 1 and 2.

Referring to FIG. 1, the present inventive apparatus, generally indicated at 10, comprises control unit 20, collection unit 30, and a signal cable 18 coupled therebetween. The collection unit 30 includes a backboard 32 and a plurality of hooks 34 mounted to an upper edge of backboard 32. Hooks 34 are adapted to be removeably placed on any suitable horizontal bar or bed frame for suspension support of unit 30.

A catheter coupler 35 is provided for coupling a standard state of the art medical urinary catheter (not shown) to input tube 36 of unit 30. Input tube 36 passes through antireflux valve 38 and then into measurement column 40. Measurement column 40 is fixed to backboard 32 by column clamps 46, and lies in a substantially vertical orientation when backboard 32 is appropriately suspended for use. From the bottom of measurement column 40, tube 36(a) passes through peristaltic pump 50 to output valve 70. Output valve 70 serves to route the urinary output to either a collection bag 90 or sample bottle 80.

The collection bag 90 is removably coupled to backboard 32 by bag hooks 92 as is well known in the art. Tube 36(b) is coupled to bag 90 through bag coupler 88, also well known in the art, so that a full collection bag 90 may be removed and replaced without spillage from tube 36(b).

Mounted on backboard 32 adjacent the upper end of measurement column 40 is an optical sensor comprising light source 41 and photodetector 43. Light source 41 and photodetector 43 are oriented so that light from light source 41 passes through measurement column 40 and strikes photodetector 43. Light source 42 and photodetector 44 and likewise mounted on backboard 32 adjacent to the bottom of measurement column 40, and are oriented so that light from light source 42 passes through measurement column 40 and strikes photodetector 44. The frequency of light transmitted by light sources 41 and 42 is chosen so as to pass through an empty column 40 but be blocked by a full column. Likewise, sample bottle 80 which is removably placed in snap clamps 78 fixed to backboard 32, has light source 82 and photodetector 84 mounted on backboard 32 on opposite sides of sample bottle 80 adjacent the top thereof. Bottle 80 is also vertically oriented when backboard 32 is appropriately suspended, and light from light source 82 will pass through bottle 80 to photodetector 84 until bottle 80 is full. A cap holder 87 may be fixed to backboard 32 adjacent bottle 80 for retension of the bottle cap 85 until bottle 80 is removed for analysis.

If automatic specimen collection is not desired, the output of pump 50 may be coupled directly to bag coupler 88, omitting valve 70, bottle 80, light source 82, photodetector 84, clamps 78, bottle cap 85, holder 87 and interlock switch 86.

Valve 70 comprises a T intersection 72, pinch blocks 74 and 75 adjacent the two tubes 36(c) and 36(b) downstream from intersection 72, and rotatable pinch bar 76. Bar 76 is rotated about pivot point 77 by a standard wellknown device such as a solenoid (not shown) which may be mounted on the reverse side of backboard 32. Bar 76 is shown pinching the tube 36(c) which leads to bottle 80 against block 74. This effectively seals tube 36(c) and forces the output of pump 50 to be directed to bag 90. Alternatively, when the bar 76 is rotated to meet block 75 as shown in phantom at 76', the tube 36(b) leading to bag 90 is blocked and tube 36(c) leading to bottle 80 is open, thereby rerouting the output of pump 50 to bottle 80.

Control unit 20 may include digital display 22, printer 24, alarm 23, control input 28, clock 26, and control logic 21 housed advantageously in one compact housing 25. Control input 28 may include manual switches such as sample collection switch 27 and master power switch 29. Control logic may advantageously comprise any standard microprocessor, such as a type 6502, with appropriate readonly memory and randomaccess memory attached, although hardwired logic designs may serve equally effectively.

The operation of the present invention may be best understood by reference to FIG. 2. Initially, pump 50 is stopped, and a fresh bag 90 and bottle 80 are attached to unit 30 as described above. Urinary output passes through catheter coupler 35 and anti-reflux valve 38 to column 40. Various signal lines are contained within signal cable 18 to couple the signal outputs of photodetectors 43, 44 and 84 as well as the output of interlock switch 86 to control logic 21. Other couplings through signal cable 18 include control lines from control logic to pump 50 and valve 70. Switch 86 is coupled to control logic 21 so that valve 70 will not direct urinary output to bottle 80 when bottle 80 is absent from the system.

Since pump 50 is initially stopped, urinary output backs up from that point through measuring column 40. Near the bottom of measuring column 40, the output will block light to photodetector 44, thus notifying control logic 21 when the fluid has reached this level. At predetermined time intervals, the pump 50 will operate to empty measuring column 40 until photodetector 44 once again receives light. A magnetic or other sensing device 51 can be used to count rollers 54 as they are rotated by the pump thus accurately determining the amount of urine transported. Alternatively, if the rate of flow of pump 50 is known, the time taken to reach an empty signal from photodetector 44 can be used to compute the amount of urinary output accumulated since the last pump operation. This computed information may be displayed on display 22 and printed by a printer 24, along with the time as indicated by clock 26. Printer 24 is advantageously loaded with paper having an adhesive backing, so that the printed record may easily be attached to the patient's chart by the attending nurse.

During operation of pump 50, valve 70 normally routes the output to bag 90. However, under predetermined conditions such as specific input from control 28, the output may be routed by valve 70 to specimen bottle 80. Control logic 21 will terminate the filling of bottle 80 by resetting valve 70 when photodetector 84 indicates that bottle 80 is full. When photodetector 44 indicates that measurement column 40 is empty, control logic 21 shuts down pump 50 until the predetermined time interval again passes. The use of an optical sensor means such as light source 82 and photodetector 84 allows the use of specimens bottles 80 of any size. Alternatively, if a bottle 80 of a single standard size is used, light source 82 and photodetector 84 may be omitted; control logic 21 then determines the point at which bottle 80 is full, based on the known flow rate of pump 50.

In the event that high urinary output occurs, measurement tube 40 may fill up prior to the passage of the predetermined time interval. If this occurs, the signal from photodetector 43 will inform control logic 21 to operate pump 50 until the column is again empty as indicated by photodetector 44. Control logic 21 again uses the time taken to empty column 40 or signals from sensor 51 to determine the amount of urinary output involved, and may display this event together with the time as previously described on display 22 and printer 24, and can also activate alarm 23 informing medical personnel of the situation. Control logic 21 also maintains a running total of urinary output routed to bag 90, so that alarm 23 may inform medical personnel when bag 90 is full. Alarm 23 may consist of, for instance, local audio outputs or remote transmissions to a nurses station, both of which are well known in the art.

Digital display 22 may be configured to display a variety of information either simultaneously or sequentially under automatic control, or sequentially under manual control. This information may include the current time of day, the volume of urinary output in the previous predetermined time interval, and the total volume currently collected in bag 90. The control input 28 may include either local or remote manual controls for power to the system, specimen collection information to be displayed on the digital display 22, and length of the aforementioned predetermined time interval.

The dimensions of the light beam projected by light sources 41, 42, and 82 should be substantially less than the diameter of column 40 or bottle 80. This will allow the light to be projected through one side of these containers and the output of tube 36 to be directed down another side of the containers, thus preventing accidental tripping of photodetectors 43, 44, or 84 by fluid flow rather than accumulated output.

Turning now to FIGS. 3 and 4, a peristaltic pump 50 is illustrated which may advantageously be incorporated in the present invention. The pump 50 includes a frame 60, a rotating disc 52, a portion of tubing 36(a), and a u-shaped pressure ring member 56.

Disc 52 is driven on axle 53 by any well-known motor (not shown) which may be mounted, for instance, on the reverse side of backboard 32. Around the periphery of disc 32 are mounted a plurality of free wheel rollers 54 with axes parallel to axle 53. The circumference of each roller 54 extends beyond the circumference of main disc 52.

Pressure ring member 56, in FIG. 3, encompasses a portion of main disc 52. The extremities of ring 56 define channels 57 facing disc 52, the channels being sufficiently wide to hold but not constrict tube 36(a). Ring 56 is coupled at pivot point 68 to arm 67, and the other end of arm 67 is coupled at pivot point 69 to handle 65. Handle 65 is rotatable about fixed pivot point 66 and may be used to engage or disengage ring 56 with tube 36(a) and disc 52. As shown in FIG. 3, ring 56 is in a fully engaged position and handle 65 is blocked from further counterclockwise rotation by stop pin 64 mounted to pump frame 60.

In FIG. 4, handle 65 has been rotated clockwise until stopped by contact with ring member 56. Ring extensions 58 which extend outward from ring member 56 is slidably engage side rails 63 of frame 60 to align the motion of ring member 56 pulled by handle 65. When the ring is re-engaged as shown in FIG. 3, the ends of ring member 56 are positioned adjacent top rail 61 of frame 60 and tube 36(a) enters and exits the pump 50 between the aforementioned channels 57 and channels 62 defined in the ends of top rail 61 adjacent channels 57. The tube 36(a) passes between ring member 56 and disc 52, and is constricted by pressure of rollers 54 against ring member 56 so that the flow of fluid through the tube is blocked. As disc 52 rotates, the passage of rollers 54 along tube 36(a) force equal pulses of fluid through the pump, although the fluid actually comes in contact only with tube 36(a).

A variety of equally useful alternative peristaltic pumps are available off-the-shelf including, for instance, Model 200 from Roll-Flex Industries of Elgin, Ill.

When ring member 56 is disengaged from tube 36(a) as shown in FIG. 4, pump 50 is disabled and tube 36(a) may be removed therefrom for cleaning or replacement. Referring again to FIG. 1, it can be seen that the entire unit 30 is modular and tube 36(a), (b), (c) and various other components can be connected and disconnected at connectors 37. This allows quick replacement of faulty components and easy disassembly for cleaning and sterilization before use of the inventive system with a new patient.

Thus, it can be seen that the present invention provides efficient collection and measurement of urinary output without the need for frequent patient monitoring by trained personnel and without the dangers and disadvantages inherent in electrical contact between the urine and prior art measurement systems. The use of a peristaltic pump and optical measurement means insures that only the catheter and tubing contacts the urine, thus reducing potential sources of contamination to a minimum. The use of adhesive paper in a printer produces a historical record of the patient's condition which is readily compatible with other human-readable records maintained in modern health care administration practice. The use of alarms allows attention to the patient or the invention by trained personnel whenever necessary rather than on a fixed, excessively redundant and wasteful schedule.

While a presently preferred form of the present invention has been disclosed, it will be appreciated that many modifications and variations thereon may be made without departing from the true spirit and scope thereof as expressed in the following claims.

What is claimed is:

1. A fluid measurement and collection apparatus, comprising a collection means adapted to collect urinary output from a patient and a microprocessor means adapted to measure urinary output in said collection means; said collection means comprising in combination, measurement column means, said measurement column means being adapted to receive and retain fluid for optical measurement, first and second optical sensor means positioned adjacent said measurement column means, said first optical sensor means being adapted to indicate whether said measurement column means is substantially empty, said second optical sensor means being adapted to indicate whether said measurement column is substantially full, pump means coupled to said measurement column means, said pump means being adapted to remove fluid from said measurement column means at a known pump flow rate, and collection bag means coupled to said pump means, said collection bag means being adapted to receive fluid removed from said measurement column means by said pump means; clock means adapted to indicate time intervals, said clock means being coupled to said microprocessor means, said first and second optical sensor means and said pump means being coupled to said microprocessor means, said microprocessor means being adapted to activate said pump means when said second optical sensor means indicates that said measurement column means is substantially full, to drain said measurement column means and measure time intervals indicated by said clock means until said first optical sensor means indicates said measurement column means is substantially empty, and to determine volume of said fluid equal to the measured time intervals multipled by the known pump flow rate.

2. The apparatus of claim 1, wherein said pump means further comprises flexible tube means adapted to convey said fluid; disc means, said disc means being rotatable and placed adjacent said flexible tube means, a plurality of freewheeling rollers, each said roller being mounted on said disc means with peripheral surfaces of each said roller extending beyond the periphery of said disc means; and ring member means, said ring member means being adapted to hold said tube means between said disc means and said ring member means to that said rollers compress said flexible tube means when brought into contact with said tube means by rotation of said disc means, to urge fluid within said tube means through said tube means ahead of said rollers.

3. The apparatus of claim 2 wherein said ring member means is removably positioned with respect to said tube means, so that disengagement of said ring member means allows for easy removal of said tube means from said pump means.

4. The apparatus of claim 3 further comprising first and second rail means, said first and second rail means being placed adjacent of said ring member means, and adapted to allow said ring member means to slidably move between said first and second rail means for engagement and disengagement of said ring member means with said tube means.

* * * * *